US00PP16544P2

(12) United States Plant Patent
Olesen

(10) Patent No.: US PP16,544 P2
(45) Date of Patent: May 16, 2006

(54) SHRUB ROSE PLANT NAMED 'POULCOT003'

(50) Latin Name: ***Rosa* hybrid**
Varietal Denomination: Poulcot003

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 73 days.

(21) Appl. No.: 11/002,743

(22) Filed: Dec. 1, 2004

(51) Int. Cl.
*A01H 5/00* (2006.01)

(52) U.S. Cl. ..... Plt./107
(58) Field of Classification Search ..... Plt./107, Plt./108, 149
See application file for complete search history.

*Primary Examiner*—Anne Marie Grunberg
*Assistant Examiner*—June Hwu

(57) ABSTRACT

A new garden rose plant of the shrub rose class which has abundant, deep pink flowers and attractive foliage. This new and distinct variety has shown to be uniform and stable in the resulting generations from asexual propagation.

2 Drawing Sheets

Botanical Classification: *Rosa* hybrid.
Variety denomination: 'Poulcot003'.

SUMMARY IF THE INVENTION

The present invention constitutes a new and distinct variety of garden rose plant that originated from a controlled crossing between the female seed parent 'Kormixal', a non-patented variety, and the male pollen parent, an unnamed seedling.

The two parents were crossed during the summer of 1995, and the resulting seeds were planted in a controlled environment in Fredensborg, Denmark. The new variety is named 'Poulcot003'.

The new variety may be distinguished from the female seed parent 'Kormixal' by a difference in flower petal color. 'Kormixal' has medium red flowers. 'Poulcot003' has deep pink flowers.

The new variety may be distinguished from its male pollen parent, an unnamed seedling, by the following combination of characteristics:

1. The male pollen parent has a flower diameter of 40 to 45 mm. 'Poulcot003' has a flower diameter of 53 mm on average.
2. The male pollen parent has fewer thorns than 'Poulcot003'.
3. The male pollen parent has light pink flowers, while 'Poulcot003' has deep pink flowers.

The objective of the hybridization of this rose variety was to create a new and distinct variety for garden use with unique qualities, such as:

1. Uniform and abundant deep pink single petal flowers;
2. Vigorous, but compact spreading growth;
3. Propagates easily from soft wood cuttings;
4. Exhibits a profusion of rose hips;
3. Exceptional disease resistance.

This combination of qualities is not present in previously available commercial cultivars of this type, known to the inventors, and distinguish 'Poulcot003' from all other varieties of which we are aware.

As part of the rose development program, Mogens N. Olesen germinated the seeds from the aforementioned hybridization during winter of 1995 and conducted evaluations on the resulting seedlings in a controlled environment in Fredensborg, Denmark.

'Poulcot003' was selected in the spring of 1996 by the inventor as a single plant from the progeny of the aforementioned hybridization.

Asexual reproduction of 'Poulcot003' by traditional budding and rooted cuttings was first done by Mogens N. Olesen in the nursery in Fredensborg, Denmark in July 1996. This initial and other subsequent asexual propagations conducted in controlled environments have demonstrated that the characteristics of 'Poulcot003' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, seed, and stems, of 'Poulcot003'. Specifically illustrated in the drawings:

FIG. 1.2; Flower bud as sepals begin to unfold;

FIG. 1.3; Open flower;

FIG. 1.4; Juvenile and mature bare stems exhibiting thorns and anthocyanic pigment;

FIG. 1.5; Sepals, receptacle, and peduncle;

FIG. 1.6; Flower petals, detached;

FIG. 1.7; Juvenile leaves, upper and lower surface;

FIG. 1.8; Mature leaves, upper surfaces;

DETAILED DESCRIPTION OF THE VARIETY

Figure 1:
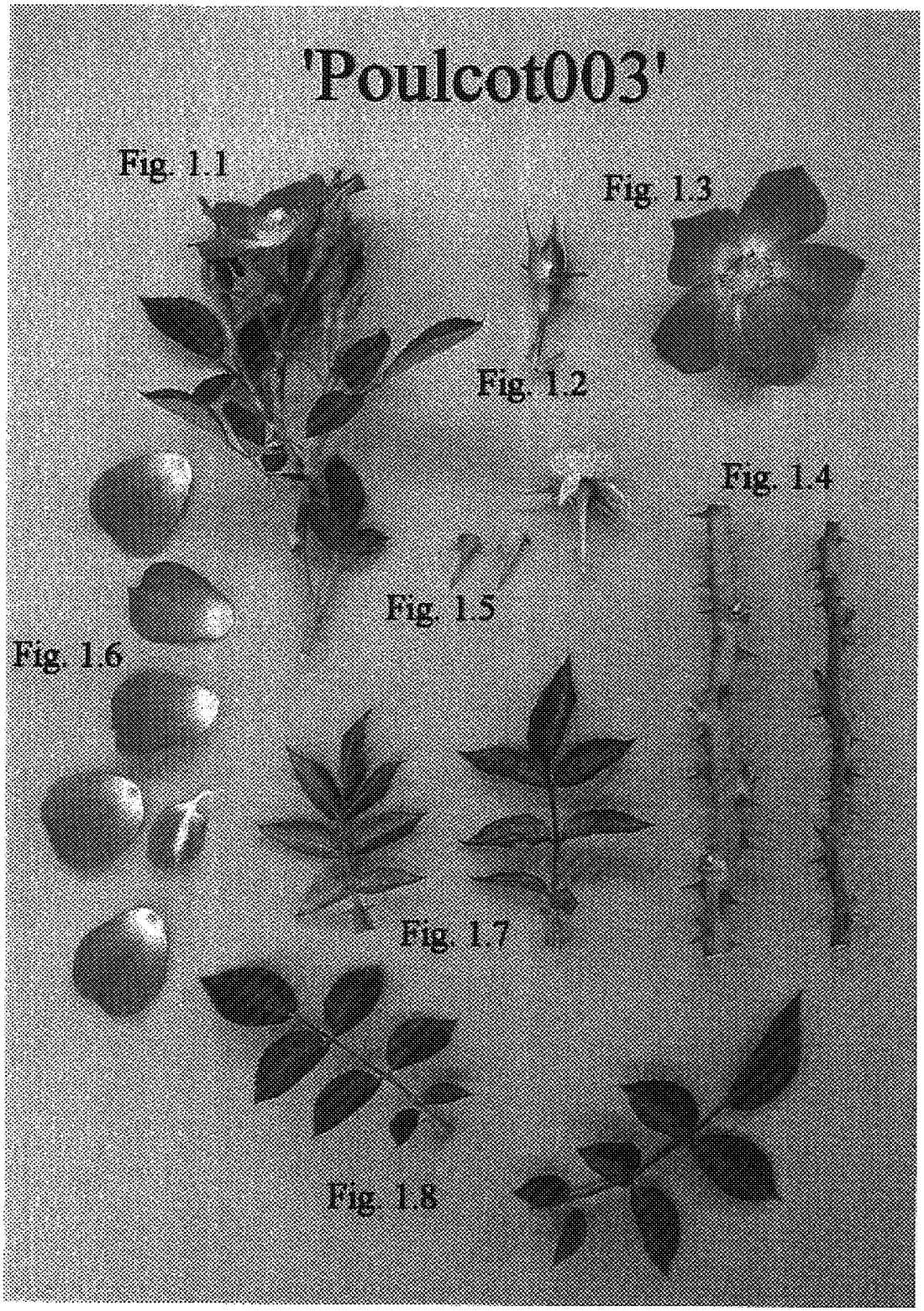
FIG. 1.1; Stem showing open flower, branching, and the attachment of leaves, buds, and peduncles.
Figure 2:
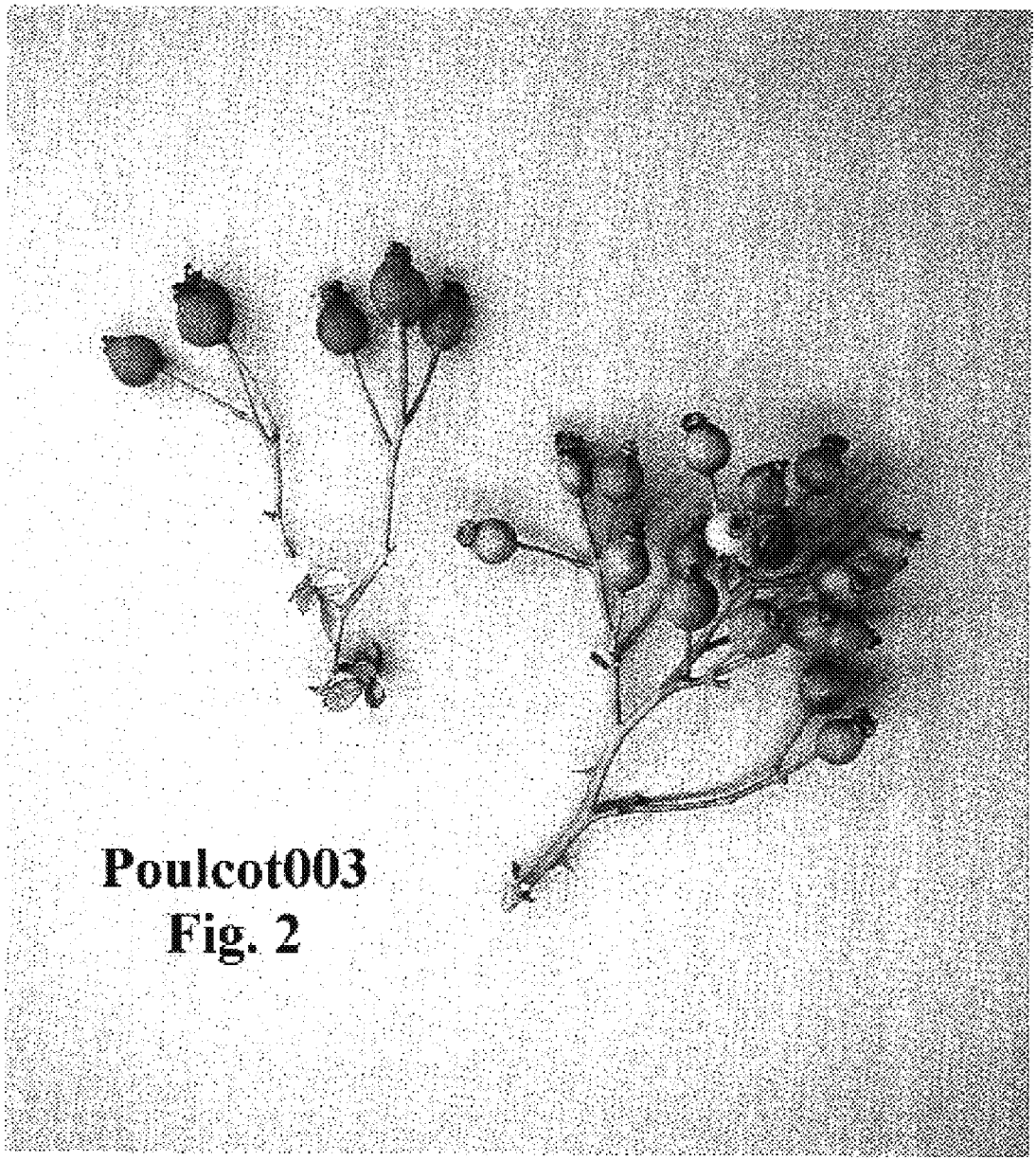
FIG. 2; Rose hips.

The following is a description of 'Poulcot003', as observed in its growth in a field nursery in Jackson County, Oreg. Observed plants are 2 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulerry', a rose variety from the same inventors described and illustrated in U.S. Plant Pat. No. 13,450 issued Jan. 7, 2003, are compared to 'Poulcot003' in Chart 1.

CHART 1

| | 'Poulcot003' | 'Poulerry' |
|---|---|---|
| General tonality. | Blend of Red Group 52A to Red-Purple Group 58B. | Red-Purple Group 58C. |
| Petalage | 6 | 12 to 14 |
| Color of filaments | Green-Yellow Group 1C | Yellow Group 3C |

FLOWER AND FLOWER BUD

Blooming habit: Continuous.

Flower bud:

*Size.*—Upon opening, 16 mm in length from base of receptacle to end of bud. Bud diameter is 6 to 7 mm.

*Bud form.*—Ovate.

*Bud color.*—As sepals unfold, petals are Red Group 53B.

*Sepal inner surface.*—Color: Yellow-Green Group 146B to Green Group 138B. Surface: Somewhat pubescent.

*Sepal outer surface.*—Color: Yellow-Green Group 146B. Anthocyanic pigments observed of Greyed-Purple 185A. Texture: Smooth to somewhat rough with few stipitate glands.

*Sepal shape.*—Apex: Cirrhose. Base: Flat at union with receptacle.

*Sepal margin.*—Margins have medium foliaceous appendages on three of the five sepals.

*Sepal size.*—18 to 20 mm (l)×6 mm (w).

*Receptacle.*—Texture: Smooth. Shape: Elliptical. Size: 6 mm (h)×5 mm (w). Color: Yellow-Green Group 144A and Green Group 138B. Anthocyanic pigments the color of Greyed-Purple 185A.

*Peduncle.*—Surface: Rough with moderate quantities of small prickles. Length: 10 to 12 mm. Diameter: 3 mm on average. Color: Yellow-Green Group 144B. Anthocyanic pigments the color of Greyed-Purple Group 182B.

*Pedicel.*—Surface: Very rough with stipitate glands. Length: 23 mm on average. Diameter: 1.5 mm on average. Color: Yellow-Green Group 144B to 144D. Anthocyanic pigments Greyed-Purple Group 185A. Strength: Weak.

Flower bud development: Flower buds are borne, in clusters of 9 to 11 flower buds per stem. Inflorescence type is a corymb.

Flower bloom:

*Fragrance.*—None.

*Duration.*—The blooms have a duration on the plant of approximately 4 to 6 days. Petals fall cleanly away from plant.

*Size.*—Flower diameter is 53 mm when open. Flower depth is 11 mm.

*Flower shape.*—Single petal type. Fully open flowers are almost flat.

Petalage: Under normal conditions, flowers have 6 petals total. Occasionally one of the petals is a petaloid.

Petal color:

*Upon opening.*—Upper surface: Red-Purple Group 58B to Red Group 52A at middle to marginal zone. Intonations of Red-Purple Group 62B to 62C at basal zone. Lower surface: Red Group 53C. Light intonations of Red Group 55C at basal zone.

*Basal petal spots, upon opening.*—Upper surface: Green-White Group 157A to Yellow Group 4D. Lower surface: Green-White Group 157A to Yellow Group 4D.

*After opening.*—Upper surface: Red-Purple Group 58B with light intonations of Red-Purple N57B. At the basal zone intonations of Red-Purple Group 62C.

*Lower surface.*—Red-Purple Group 61C to Red-Purple Group 58B. Intonations of Red-Purple Group N57C at basal zone. Occasionally petals exhibit streaks of Red-Purple Group 65C.

*Basal petal spots, upon opening.*—Upper surface: White Group 155D. Lower surface: White Group 155D.

General tonality: On open flower a blend of Red Group 52A to Red-Purple Group 58B. No changes in tonality observed.

Petals:

*Petal reflex.*—Flat.

*Margin.*—Entire, with an occasional point at the center.

*Shape.*—Narrow elliptic. Apex: Rounded. Base: Acute.

*Size.*—27 mm (l)×21 mm (w).

*Texture.*—Smooth.

*Thickness.*—Thin.

Petaloids:

*Quantity.*—1.

*Size.*—22 mm (l)×13 mm (w).

*Shape.*—Generally narrow elliptical. Apex: Rounded. Base: Very acute.

*Color.*—Upper surface: Red-Purple Group 58B with light intonations of Red-Purple N57B. At basal zone intonations of Red-Purple group 62C. Occasionally petal streaking of White Group 155D bisecting the petaloid. Lower surface: Red-Purple Group 61C to Red-Purple Group 58B. Intonations of Red-Purple Group N57C at basal zone. Occasionally streaks of Red-Purple Group 65C and White Group 155D bisecting petaloids.

Reproductive organs:

*Pollen.*—Quantity: Abundant. Color: Yellow-Orange Group 21B to 22A.

*Anthers.*—Size: 1.5 mm in length. Color: Yellow-Orange Group 22A to 21B. Quantity: 75 on average.

*Filaments.*—Color: Yellow Group 3C. Length: 4 mm.

*Pistils.*—Length: 5 mm. Quantity: 25 on average.

*Stigmas.*—Level in location relative to the length of the filaments and the height of the anthers. Color: Yellow-Green Group 145C to 145D.

*Styles.*—Color: Yellow-Green Group 145C to 145D.

*Hips.*—Size: Normally 14 mm in height by 11 mm wide. Shape: Rounded to somewhat elliptical. Color: Greyed-Orange Group 169A. Number of seed: 10 to 20.

PLANT

Plant growth: Spreading and low growing shrub. When grown as a budded field grown plant on *Rosa multiflora* understock, the average height of the plant is 35 to 45 cm and the average width is 50 to 75 cm.

Stems:

*Color:* Juvenile growth: Green Group 138B to Yellow-Green Group 146C. Anthocyanic intonations of Greyed-Red 182B to Greyed-Purple 184B. Mature growth: Yellow Green Group 146B.

*Length.*—On average, canes are 30 to 40 cm from the base of the plant to the flowering portion.

*Diameter.*—6 mm.

*Internodes.*—On mature canes, there is an average distance of 23 mm between nodes.

*Surface texture.*—Young wood: Rough with prickles. Older wood: Smooth.

Thorns:

*Incidence.*—10 to 20 thorns per 10 cm of stem on average.

*Size.*—7 mm in length.

*Shape.*—Upper side: Flat. Lower side: Deeply concave.

*Color.*—Juvenile thorns are Greyed-Red Group 179A.

Plant foliage: Normally 7 leaflets on leaves in middle of the stem.

*Compound leaf.*—80 mm (l)×50 mm (w).

*Quantity.*—4 leaves per 10 cm of stem on average.

*Color of mature foliage.*—Upper side: Yellow-Green Group 147A. Lower side: Yellow-Green Group 147B.

*Color of juvenile foliage.*—Upper side: Yellow-Green Group 146B. Greyed-Purple Group 183A. at margins. Lower side: Yellow-Green Group 146B with Greyed-Purple Group 183A generalized.

Plant leaves and leaflets:

*Stipules.*—Size: 10 mm in length. Shape: Linear, slightly broad based with outward extending apecies. Margins: Finely serrated with many stipitate glands. Color: Yellow-Green Group 146A.

*Petiole.*—Length: 12 mm. Diameter: 2 mm.

*Upper surface.*—Color: Yellow-Green Group 146A. Observations: Few stipitate glands on the upper side margins.

*Lower surface.*—Color: Yellow-Green Group 146C. Rachis: Length: 40 mm. Upper surface: Color: Yellow-Green Group 146A. Observations: Stipitate glands. Lower surface: Color: Yellow-Green Group 146C. Observations: Small prickles. Leaflet: Edge: Serrated. Size: Average size of the terminal leaflet on normal leaves is 30 mm (l)×18 mm (w). Shape: Elliptical. Base: Obtuse. Apex: Acuminate. Texture: Smooth. Thickness: Thick. Arrangement: Odd pinnate. Venation: Reticulate. Glossiness: Somewhat glossy.

Disease resistance: Above average resistance to powdery and downey mildews, rust, black spot, and *Botrytis* under normal growing conditions in Jackson County, Oreg.

Cold hardiness: The variety 'Poulcot003' has been found to be cold tolerant to USDA Cold Hardiness Zone 6.

What is claimed:

1. A new and distinct variety of rose plant of the shrub rose class named 'Poulcot003', substantially as illustrated and described herein as a distinct and novel rose variety due to its abundant deep pink flowers, disease resistance and extended period of bloom.

* * * * *

'Poulcot003'
Fig. 1.1
Fig. 1.2
Fig. 1.3
Fig. 1.4
Fig. 1.5
Fig. 1.6
Fig. 1.7
Fig. 1.8

Poulcot003